(12) United States Patent
Slone

(10) Patent No.: US 6,231,016 B1
(45) Date of Patent: May 15, 2001

(54) MEDICAL SUPPORT CARRIER

(76) Inventor: Beth A. Slone, 136 LeGrande Blvd., Gallipolis, OH (US) 45631

( * ) Notice: Subject to any disclaimer, the term of this patent is extended or adjusted under 35 U.S.C. 154(b) by 0 days.

(21) Appl. No.: 09/589,190

(22) Filed: Jun. 8, 2000

Related U.S. Application Data

(60) Provisional application No. 60/138,278, filed on Jun. 9, 1999.

(51) Int. Cl.[7] .................................................. E04G 25/00
(52) U.S. Cl. .................................... 248/200.1; 248/125.8; 248/229.13; 280/304.1
(58) Field of Search ........................... 248/200.1, 201, 248/213.2, 225.52, 229.23, 229.24, 227.3, 231.61, 316.8, 122.1, 124.1, 125.8, 229.22, 230.3, 230.5, 231.41, 298.1; 280/304.1

(56) References Cited

U.S. PATENT DOCUMENTS

| Re. 22,824 | * | 12/1946 | Morehouse | 248/74.3 |
|---|---|---|---|---|
| 2,818,910 | * | 1/1958 | Hawkins | 297/45 |
| 2,957,187 | | 10/1960 | Raia . | |
| 3,709,556 | | 1/1973 | Allard et al. . | |
| 3,891,268 | * | 6/1975 | Taylor | 5/81.1 R |
| 4,431,206 | | 2/1984 | Pryor . | |
| 4,506,903 | * | 3/1985 | Bowsermaster | 280/304.1 |
| 4,511,157 | | 4/1985 | Wilt, Jr. . | |
| 4,754,946 | * | 7/1988 | Constantin | 248/503.1 |
| 4,969,768 | * | 11/1990 | Young | 403/97 |
| 5,016,307 | * | 5/1991 | Rebar | 5/503 |
| 5,094,418 | | 3/1992 | McBarnes, Jr. et al. . | |
| 5,135,191 | | 8/1992 | Schmuhl . | |
| 5,180,181 | * | 1/1993 | Letechipia | 280/304.1 |
| 5,219,139 | | 6/1993 | Hertzler et al. . | |
| 5,236,213 | | 8/1993 | Trickett . | |
| 5,374,074 | * | 12/1994 | Smith | 280/304.1 |
| 5,482,239 | * | 1/1996 | Smith | 248/229.13 |
| 5,509,680 | * | 4/1996 | Scharf et al. | 280/304.1 |
| 5,556,065 | * | 9/1996 | Wadley | 248/129 |
| 5,964,439 | * | 10/1999 | Johnson | 248/278.1 |

* cited by examiner

Primary Examiner—Anita M. King
(74) Attorney, Agent, or Firm—Richard C. Litman

(57) ABSTRACT

A medical support carrier unit that holds medical equipment attached to a person bound to a wheelchair. The medical support carrier is attached to the back frame of a wheelchair. The medical support carrier includes an upper and lower set of vertical frame grippers, a turnbuckle connecting each set of grippers, vertical telescoping IV holders attached to the ends of the turnbuckles, and telescoping IV poles secured within the IV holders. The turnbuckles can be rotated to loosen and tighten the vertical frame grippers to the back of the wheelchair. The telescopic IV poles are detachable from the IV holders. The IV holders are attached to the turnbuckles by pivoting pins which allow free rotational movement when the turnbuckles are separately adjusted. The turnbuckles and IV holders essentially permit the medical support carrier as a unit to adjust both vertically and horizontally.

10 Claims, 3 Drawing Sheets

MEDICAL SUPPORT CARRIER

CROSS-REFERENCE TO RELATED APPLICATION

This application claims the benefit of U.S. Provisional Patent Application Ser. No. 60/138,278, filed Jun. 9, 1999.

BACKGROUND OF THE INVENTION

1. Field of the Invention

The present invention relates to medical support carrier having an IV pole which is mounted on the back of a wheelchair frame and, more specifically, to a multi-section pole movable between an upright position and a foldable storage position.

2. Description of Related Art

Medical equipment which has to be attached to a person bound to a wheelchair limits the patient's mobility to move freely in a wheelchair. In general, most wheelchair patients are asked to hold onto free standing intravenous (IV) stands while they are being pushed along. Some patients may not be able to hold on to a movable IV stand due to their illness or age. Also, some patients need both hands to move the wheelchair themselves and would not be able to hold onto a movable IV stand. IV pumps are designed to be clamped to various sized IV stands and poles. Often it is difficult for the pusher of a wheelchair to operate a wheelchair when IV bags/bottles and IV pumps are obstructing their view.

Due to these problem poles that hold IV solution bottles and other medical equipment have been the subject of earlier patents. Several earlier patents have altered an existing wheel-based IV stand to attach to the wheelchair frame, thereby holding the IV stand a fixed distance from the wheel chair. However, if the IV stand is attached in this fashion, the stand must be removed from the wheelchair to travel through narrow or low doorways, or to be transported into ambulances.

U.S. Pat. No. 3,709,556, issued to Allard et al. on Jan. 9, 1973, describes an IV holder in the shape of an upright pole attached to portable patient conveyances such as wheelchairs and gurneys. The holder consists of an elongated tubular base, elongated tubular extension members arranged upright which can be adjusted in height in a number of positions, and brackets for attachment to the frame of the wheelchair. The holder is attached to the bottom frame member of the wheelchair. Hook shaped members are mounted on the distal end and mid-area of the upper tubular extension members for holding intravenous solution bottles.

A major problem with this type of IV holder is that not all wheelchairs have bottom frame members for attaching the tubular base. This limits the IV holder to wheelchairs with bottom frame members. This patent is also limited to holding only IV containers. The IV holder can be mounted on either side of the chair frame, however, the user must disassemble the lower tubular member and reassemble the structure on the other side of the wheelchair frame.

An IV holder needs to be attached to the wheelchair in a manner that avoids altering the natural balance of the wheelchair, to avoid causing the chair to tip or fall over. IV stands and interchangeable holders can inflict trauma to patients when an IV stand tips over or when detachable holders are moved from one side of the wheelchair frame member to the other. When IV stands and holders are moved in the above fashion, IV needles have been known to be pulled out of the patient's arms. An ideal apparatus would allow the user to be able to attach the upper detachable IV holder to either side of the wheelchair without excessive assembly.

U.S. Pat. No. 4,431,206, issued to John Pryor on Feb. 14, 1984, describes a medical accessory carrier for mounting on a wheelchair. The carrier includes a vertical lower post, a detachable upper post, and a detachable clamp for mounting to the bottom frame member of the wheelchair. This invention requires the use of retaining screws to discourage theft of the carrier. A problem with retaining screws is that the operator must have access to the key at all times. This may especially be a problem in hospital situations where emergencies occur quite frequently. If a key is lost or not easily accessible, it could endanger a patient's life.

Other patents have proposed attaching IV holders to the vertical frame members of wheelchairs. However, this poses a major problem because not all wheelchairs have vertical frame members that will support the above IV holders. U.S. Pat. No. 5,135,191, issued to James Schmuhl on Aug. 4, 1992, describes a pole for supporting IV equipment. The elongated pole comprises two different diameters with the upper pole designed to be interchangeably used with IV stands, hospital gurneys, and wheelchairs. The lower support pole is either attached to an IV stand or a vertical frame member of a wheelchair or gurney. Motorized and self-propelled wheelchairs are made in a variety of shapes and sizes.

There have been many compatibility problems associated with other patents of IV holders and their attachment to the various styles of wheelchairs that are manufactured. An ideal IV holder would not limit its use to IV bags. Other medical equipment such as a pump monitor needs to be suspended on a holder apparatus for easy transportation as well. What is needed is an IV holder which is compatible with various styles of motorized and self-propelled wheelchairs.

None of the above inventions and patents, taken either singly or in combination, is seen to describe the instant invention as claimed.

SUMMARY OF THE INVENTION

The present invention is a medical support carrier that attaches to the back frame of a wheelchair. The medical support carrier is designed to hold medical equipment that is attached to a person bound to a wheelchair. The medical support carrier includes an upper and lower set of vertical frame grippers, a turnbuckle connecting each set of grippers, vertical telescoping IV holders attached to the ends of the turnbuckles, and telescoping IV poles secured within the IV holders.

The turnbuckles include two outer rods having external threads, each connected to opposite ends of a larger, hollow, internally threaded middle sleeve. The threads turn in opposite directions, thereby permitting the outer rods to be extended or retracted by rotating the sleeve. Extending the outer rods loosens the vertical frame grippers, while retracting the outer rods secures the vertical frame grippers to the back of the wheelchair. The vertical frame grippers include a vertical cylindrical recess on its inner surface which can be lined with a rubber or rubber like material.

The telescopic IV poles are detachable from the IV holders and can be transferred to either a gurney or IV stand. The telescoping IV poles include wing finger holds at their upper ends, with a perpendicular threaded hole passing through one finger. A threaded thumb screw fits within the hole, securing the next innermost telescoping member against the opposite finger to hold that telescoping member in place.

The IV holders are attached to the turnbuckles by pivoting pins which allow free rotational movement when the turnbuckles are separately adjusted. The turnbuckles and IV holders essentially permit the medical support carrier to adjust both vertically and horizontally.

The present invention is compatible with standard IV poles and stands which are sized to receive a clamp positioned on the back of a feeding pump. Additionally, the medical support carrier includes detachable tilt bars which prevent the wheelchair from tipping or tilting.

To install the medical support carrier, the installer grabs each turnbuckle sleeve with their hands. Then the installer positions the medical support carrier in the desired position on the back frame of the wheel chair. While holding the lower turnbuckle sleeve with one hand, the other hand rotates the upper turnbuckle sleeve until the upper vertical grippers fit snugly onto the upper back frame of the wheelchair. The lower turnbuckle sleeve is then rotated to secure the lower vertical grippers to the wheelchair frame.

Accordingly, it is a principal object of the invention to attach and position medical equipment on a wheelchair so that a person bound to a wheelchair has the freedom and mobility to travel from place to place.

It is another object of the invention to provide a medical carrier that is be compatible with almost any back frame of a wheelchair.

It is a further object of the invention to prevent medical equipment attached to a person bound to a wheelchair from obstructing the view a person pushing the wheelchair.

Still another object of the invention is to prevent the wheelchair from tipping or tilting when medical equipment is attached to the back of the wheelchair.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
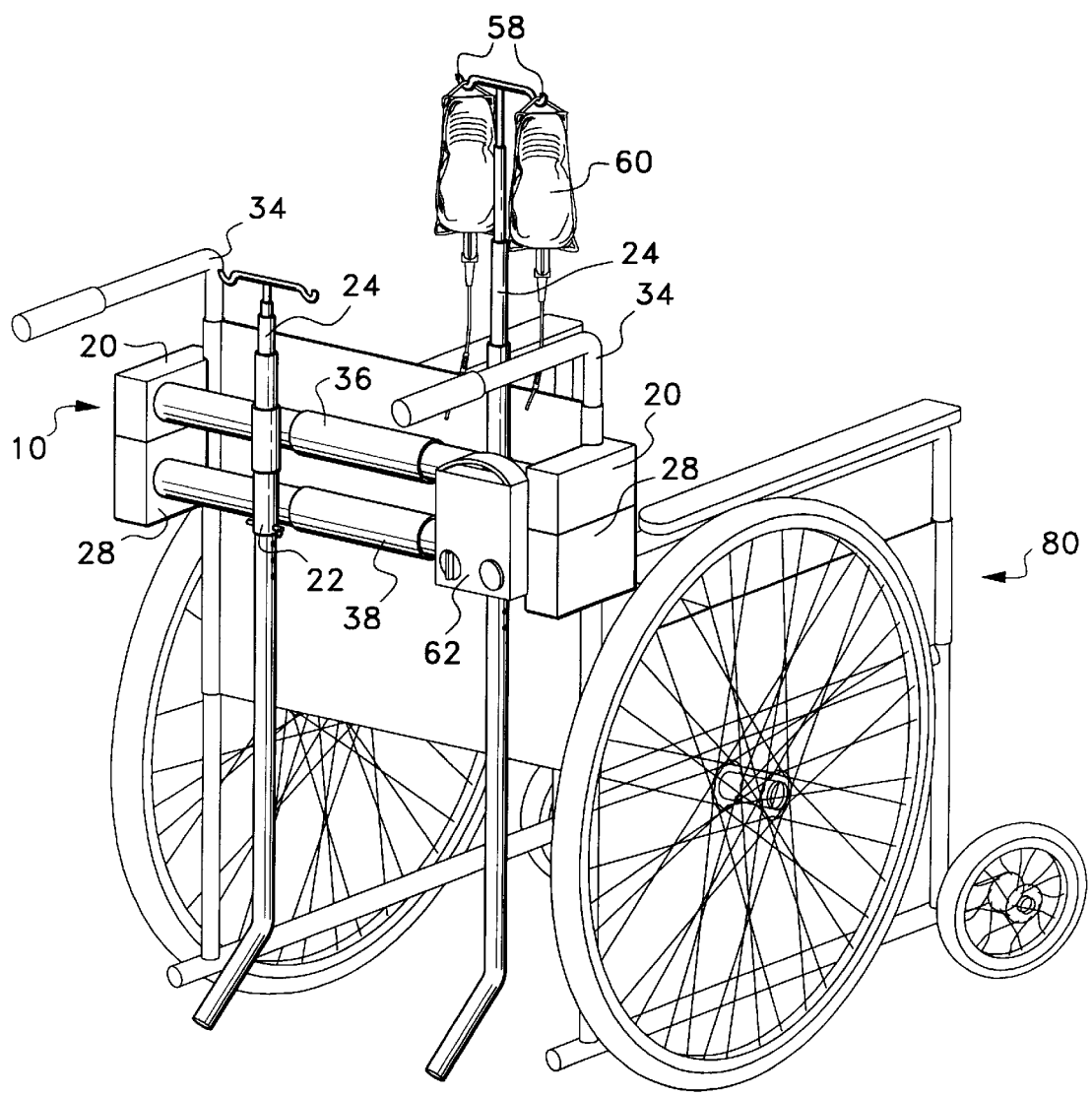
FIG. 1 is an environmental, perspective of a medical support carrier installed on the back frame of a wheelchair according to the present invention.
Figure 2:
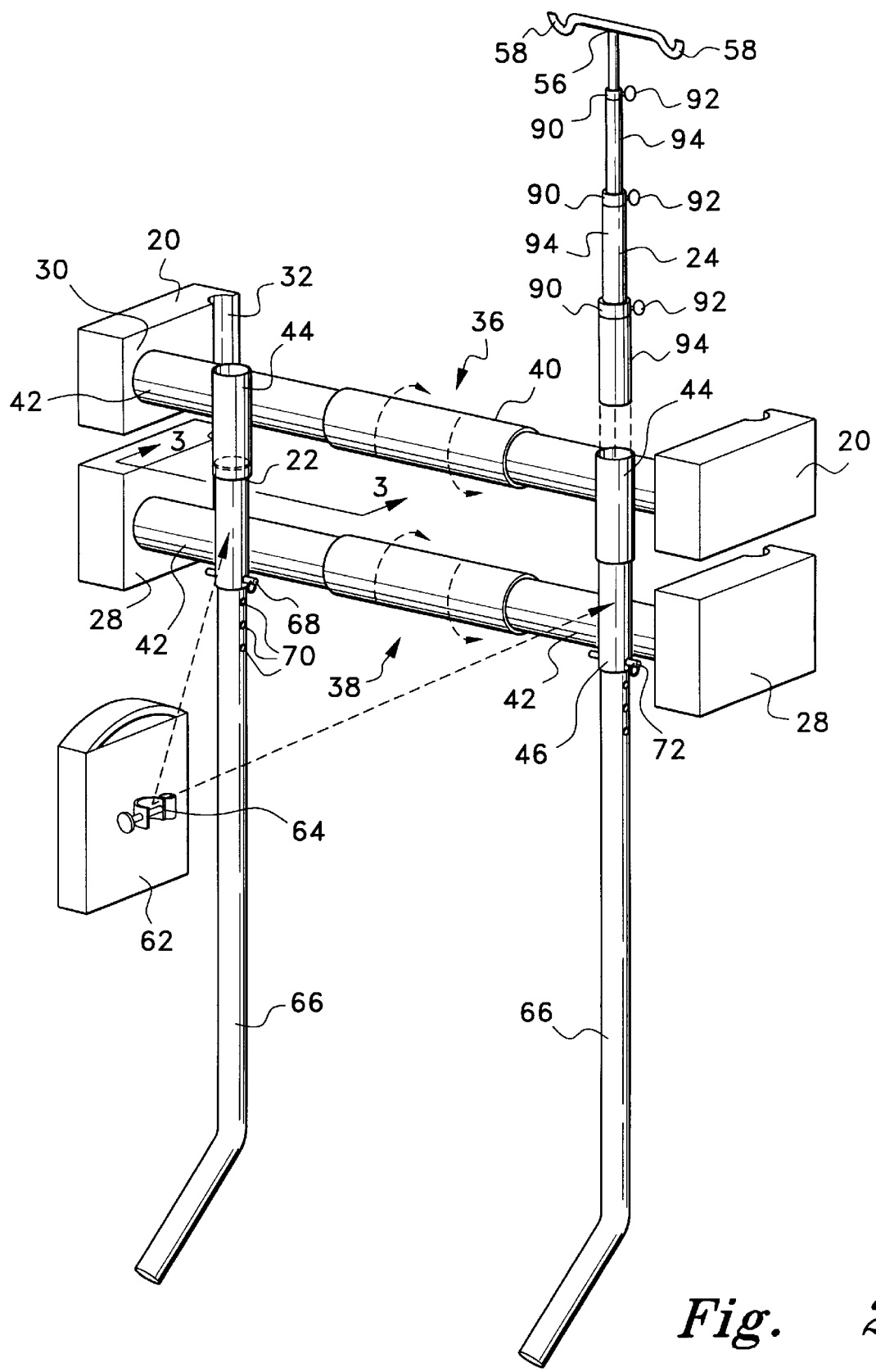
FIG. 2 is a partially exploded perspective of a medical support carrier of the present invention.

Referring to FIGS. 1–2, the present invention is a medical support carrier, designated as 10 in the drawings. The medical support carrier 10 comprises vertical gripping means, preferably in the form of upper 20 and lower 28 sets of vertical frame grippers. The medical support carrier 10 also comprises an adjustable support mechanisms, preferably in the form of an upper 36 and lower 38 horizontal turnbuckle respectively connecting between each set of grippers 20 and 28, a pole holding means, preferably in the form of vertical telescoping IV holders 22 pivotally attach to the turnbuckles 36 and 38, and intravenous holding means, preferably in the form of telescoping IV poles 24 which are held within the IV holders 22.

The vertical frame grippers 20 and 28 shown in FIG. 2 are rectangular in shape and made of a light weight sturdy material. The inner surface 30 of the vertical grippers 20 and 28 contain a vertical partial cylindrical recess 32 lined with rubber or other resilient material. The partial cylindrical recess 32 of the vertical frame grippers 20 and 28 are dimensioned and configured to fit snugly on the back frame 34 a wheelchair 80. An upper 36 and lower 38 turnbuckle make up the support structures that connect each set of frame grippers together 20 and 28.

The turnbuckles 36 and 38 includes a hollow, internally threaded central sleeve 40. The threads turn in opposing directions on opposite ends of the sleeve 40, and are sized to receive a similar externally threaded narrow outer rod 42. The outermost ends of the rods 42 of the turnbuckle 36 and 38 are attached to the inner surface 30 of the vertical frame grippers 20 and 28. When the sleeves 40 of the turnbuckles 36 and 38 are rotated, the rods 42 are extended or retracted relative to the sleeve 40, thereby securing or unsecuring the vertical frame grippers 20 and 28 onto the back frame 34 of the wheelchair 80.

Figure 3:
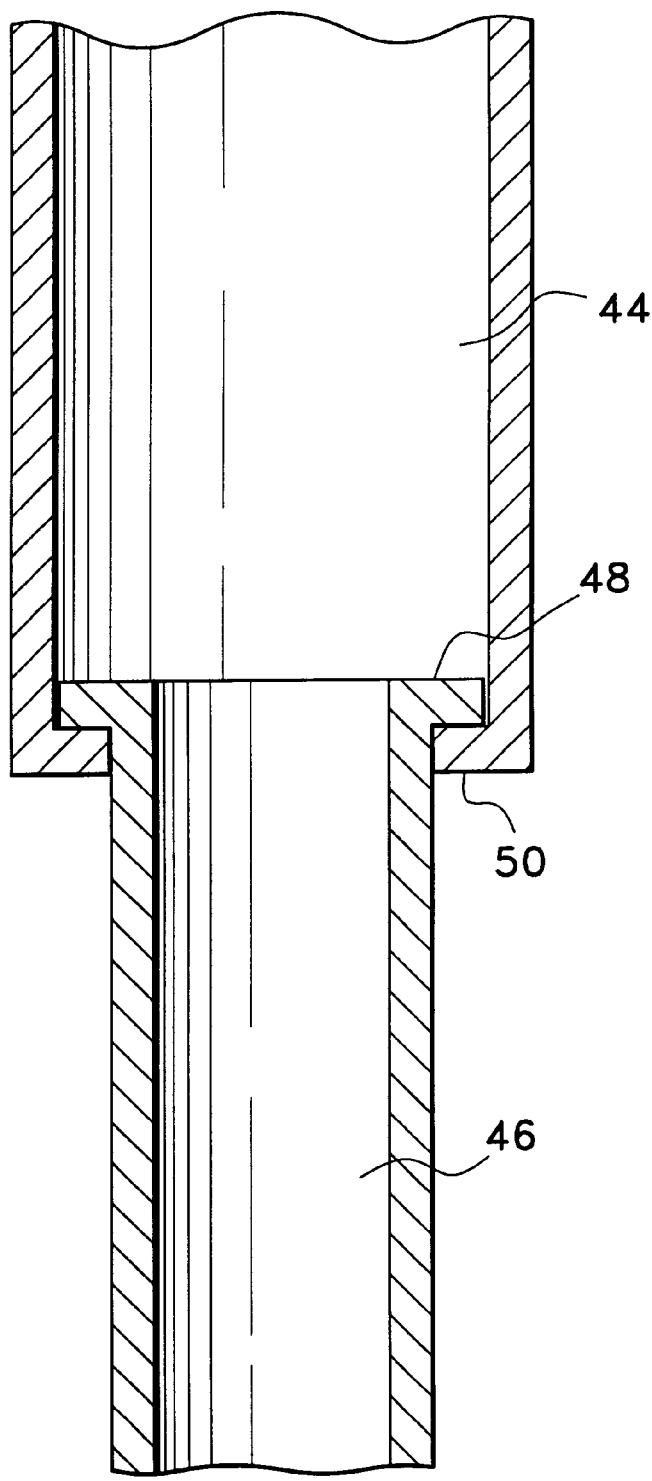
FIG. 3 is a section view of the IV holder along lines 3—3 in FIG. 2.

The IV holders 22 comprise an upper elongated tube 44 and a lower narrower elongated tube 46. The IV holders 22 are telescopic whereby the lower tube 46 can slide in and out of the upper tube 44 thereby making the IV holder 22 longer or shorter. Referring to FIG. 3, at the juncture between the upper 44 and lower 46 tube, the lower tube 46 end comprises an outward collar 48 and the upper tube 44 end comprises an inward collar 50. Together the collars 48 and 50 function to stop the upper 44 and lower 46 tube from separating when the tubes 44 and 46 are extended to their full telescopic length. Referring back to FIG. 2, the IV holders 22 are attached to the outer poles 42 of the upper 36 and lower 38 turnbuckles by a pivoting pin (not shown) that permits the IV holders 22 to be slightly rotated when the turnbuckles 36 and 38 are not simultaneously rotated. Sometimes the back frame 34 of the wheelchair 80 are not parallel to each other and a pivoting pin allows each turnbuckle 36 and 38 to be utilized separately.

The medical support carrier 10 comprises two detachable telescopic IV poles 24 which fit into the IV holders 22 which are attached to the turnbuckles 36 and 38. At diametrically opposed locations upon the head 56 of the upper IV pole 24 are hooks 58 and these hooks 58 may be attached to the head 56 by rivets, screws or the like. Shown in FIG. 1 the hooks 58 provide support for mounting an IV bottle or bag 60. Each IV pole 24 comprises a plurality of concentric elongated tubes 94, dimensioned and configured to telescope relative to each other. FIG. 3 shows the ends of elongated tubes 94, wherein an outward collar 48 abuts an inward collar 50. Together the collars 48 and 50 function to stop the telescopic tubes of the IV poles 24 from separating when the tubes are extended to their full telescopic length. The IV poles 24 additionally include a selective locking means dimensioned and configured for holding the concentric elongated tubes 94 at varying elevations. The telescoping IV poles 24 can be standard operating models used in the industry. The upper end of each elongated tube 94 of the IV poles 24 shown in FIG. 2 preferably includes wing finger holds 90 at their upper ends, with a perpendicular threaded hole passing through one finger. A threaded thumb screw 92 fits within the hole, securing the next innermost elongated tube 94 against the opposite finger to hold that elongated tube 94 in place.

Together the turnbuckles 36 and 38 with the telescoping IV holders 22 essentially permit the medical support carrier 10 as a unit to expand in a vertical or horizontal direction.

Some wheelchair back frames 34 are not necessarily parallel to each other. The turnbuckles 36 and 38 separately operate to adjust the medical support carrier 10 horizontally when the back frame 34 is not parallel. The medical accessory carrier 10 unit is designed to adjust to almost any wheelchair back frame 34.

When the turnbuckles 36 and 38 are separately adjusted, the pivoting pins through the IV holders 22 permit free rotation of the holders 22 on the outer pole 42 of the turnbuckles 36 and 38. When space is needed to clamp a pump 62 to the IV holders 22, the telescoping IV holders 22 function to adjust the length of the medical support carrier 10 in a vertical direction. By clamping a pump 62 to an IV holder 22 behind the back frame 34 of the wheelchair 80, the person pushing the wheelchair 80 does not have their view obstructed, as contrasted to having the pump 62 clamped to an IV pole 24.

The entire medical support carrier 10 unit is preferably made of a lightweight material. The IV holders 22, IV poles 24, and turnbuckles 36 and 38 is preferably hollow and made out of a sturdy material.

The present invention 10 will be compatible with standard IV poles, which are sized to receive a clamp 64 positioned on the back of an IV pump 62. The IV pump 62 will be referred to as the "pump" 62. The IV holders 22 on the present invention 10 are sized to support a standard pump 62 by means of a clamp 64 located on the back side of the pump 62. The pump 62 may be attached to the IV pole 24 so the pump 62 does not have to be unclamped from the IV holders 22 when the IV pole 24 is transported elsewhere. However, if the pump 62 does not have to be removed from the medical support carrier 10, the desirable position for attachment would be to clamp the pump 62 to the IV holder 22. The position of the pump 62 on the IV holder 22 is desirable because the pump 62 would not block the view of the person pushing the wheelchair 80.

To install the medical support carrier 10, the installer grabs each sleeve 40 of turnbuckles 36 and 38 with their hands. Then the installer positions the medical support carrier 10 to the desired position on the back frame 34 of the wheel chair 80. While holding the lower turnbuckle 38 with one hand, the other hand rotates the upper turnbuckle 36 until the upper vertical grippers 20 fit snugly onto the upper back frame 34 of the wheelchair 80. After the upper turnbuckle 36 has secured a tight fit of the upper vertical grippers 20 on the back frame 34, the other hand rotates the lower turnbuckle 38 until the lower vertical grippers 28 are also secured. Once the medical support carrier 10 is installed, the upper 36 or lower 38 turnbuckles can be rotated to loosen the vertical grippers 20 or 28 to adjust the carrier 10 vertically which is permitted by the telescoping IV holders 22. The telescoping IV holders 22 are designed to elongate, however, the elongation is limited to a certain length whereby an inward collar 50 on the end of the lower tube is stopped by a outward collar 48 on the end of the upper tube.

The medical support carrier 10 comes with tilt prevention means, preferably in the form of detachable tilt bars 66 which extend downwards from the bottom of the IV holders 22 and prevent the wheelchair 80 from tipping or tilting. The tilt bars 66 comprise an elongated tube which is narrower than the lower tube of the IV holders 22. The lower portion of the tilt bars 66 are bent. When the tilt bars 66 are installed, the lower portion of the elongated tube is bent outward extending away from the back of the wheelchair 80. The attachment mechanism includes apertures 68 located adjacent from one another on the lower end of the IV holders 22.

The upper narrower end of the tilt bars 66 have similar apertures 70 that match up when the upper narrower tilt bar 66 end slides into the larger IV holder 22 bottom tube. The tilt bars 66 have several sets of apertures 70 along the upper portion of the tube. When the upper end of the apertures 70 are lined up with the lower IV holder 22 tube apertures 68 a bolt 72 slides through corresponding apertures 68 and 70. One end of the bolt 72 has a head large enough to stop that end of the bolt 72 from sliding all the way through the attachment and has a chain connected the head of the bolt 72. The other end of the bolt 72 has an aperture designed to accept a clip (not shown), when inserted, will secure the bolt 72 in place.

The medical support carrier 10 has several advantages. The first advantage is that the carrier 10 can adjust to almost any back frame 34 of a wheelchair 80. Earlier patents have the pump 62 clamped to the IV poles 24, thereby blocking the pusher's view The second advantage of the present invention 10 would be the location of the pump 62 on the IV holder 22 because it would not block the view of the person pushing the wheelchair 80. Some wheelchairs 80 do not come with tilt bars 66 which prevent the wheelchair 80 from tipping and they are very expensive if ordered separately. A third advantage includes detachable tilt bars 66 extending out from the bottom of the IV holders 22. An IV pole is usually attached to one side of the wheelchair 80. This is a problem when the IV pole is attached to the left side of the wheelchair frame and the patient has an IV apparatus attached to the right arm. The fourth advantage of the medical support carrier 10 allows for the IV pole 24 to be inserted on the left side, right side, or both at the same time. The IV poles 24 can be lowered instead of being removed so that the wheelchair 80 can travel through narrow or low doorways. A fifth advantage of the medical support carrier 10 is that the patient may wheel themselves around without having to worry about holding a portable IV stand.

In accordance with the present invention 10, the IV pole 24 together with the intravenous bag 60 and pump 62 can be removed quickly and easily from medical support carrier's IV holder 22 to a IV stand or gurney cart.

It is to be understood that the present invention is not limited to the sole embodiment described above, but encompasses any and all embodiments within the scope of the following claims.

I claim:

1. A medical support carrier for a wheelchair, said carrier comprising:
    at least one set of vertical gripping means for attachment to the back frame of the wheelchair, an adjustable support mechanism connecting said at least one set of vertical gripping means;
    at least one intravenous holding means for holding an intravenous feeding container, said at least one intravenous holding means having an upper end;
    at least one pole holding means movably attached to said adjustable support mechanism for supporting said at least one intravenous holding means; and
    tilt prevention means depending from and secured within said at least one pole holding means for preventing the wheelchair from tipping over or tilting.

2. The medical support carrier for a wheelchair according to claim 1, wherein said adjustable support mechanism comprises a turnbuckle.

3. The medical support carrier for a wheelchair according to claim 1, wherein said at least one set of said vertical gripping means includes an inner surface defining a vertical cylindrical recess.

4. The medical support carrier for a wheelchair according to claim 1, wherein said at least one intravenous holding means comprises a plurality of concentric elongated tubes dimensioned and configured to telescopically interfit relative to each other.

5. The medical support carrier for a wheelchair according to claim 4, further comprising a selective locking means dimensioned and configured for holding said concentric elongated tubes at selected elevations.

6. The medical support carrier for a wheelchair according to claim 1, wherein the upper end of said at least one intravenous holding means includes a hook shaped member.

7. The medical support carrier for a wheelchair according to claim 1, said at least one pole holding means comprising a plurality of tubes, said tubes being dimensioned and configured for telescopically interfitting.

8. The medical support carrier for a wheelchair according to claim 7, wherein said tubes are dimensioned and configured to receive a pump.

9. The medical support carrier for a wheelchair according to claim 1, wherein said tilt prevention means comprise tilt bars extending downward from said at least one pole holding means.

10. The medical support carrier for a wheelchair according to claim 1, wherein the medical support carrier is constructed of sturdy materials that are light in weight.

\* \* \* \* \*